United States Patent [19]

Greber et al.

[11] Patent Number: 5,126,462
[45] Date of Patent: Jun. 30, 1992

[54] SULFUR-CONTAINING AROMATIC TETRACARBOXYLIC ACIDS AND DERIVATIVES THEREOF

[75] Inventors: Gerd Greber, Bad Vöslau; Heinrich Gruber; Marcel Sychra, both of Vienna, all of Austria

[73] Assignee: Chemie Linz Gesellschaft m.b.H., Linz, Austria

[21] Appl. No.: 466,435

[22] PCT Filed: Nov. 10, 1988

[86] PCT No.: PCT/EP88/01017
§ 371 Date: Jun. 12, 1990
§ 102(e) Date: Jun. 12, 1990

[87] PCT Pub. No.: WO89/04298
PCT Pub. Date: May 18, 1989

[30] Foreign Application Priority Data

Nov. 12, 1987 [DE] Fed. Rep. of Germany ....... 3738456

[51] Int. Cl.$^5$ ............... C07D 307/77; C07C 315/04; C07C 317/32; C07C 51/60
[52] U.S. Cl. ...................... 549/241; 528/352; 549/242; 560/13; 562/427; 562/430; 562/840
[58] Field of Search .............. 549/241, 242; 560/13; 562/427, 430, 840

[56] References Cited

U.S. PATENT DOCUMENTS

| | | | |
|---|---|---|---|
| 3,895,064 | 7/1975 | Brode et al. | 564/315 |
| 4,255,313 | 3/1981 | Antonoplos et al. | 560/13 X |
| 4,621,134 | 11/1986 | Aritomi et al. | 528/337 |
| 4,724,257 | 2/1988 | Aritomi et al. | 528/352 |

OTHER PUBLICATIONS

Skroog et al., "Macromol. Revs." 11 161-208 (1976).
Skroog et al., "J. Polym. Sci." 3A 1373-1390 (1965).
Sheffer, "J. Appl. Polym. Sci." 26 3837-3843 (1981).

*Primary Examiner*—José G. Dees
*Assistant Examiner*—Vera C. Clarke
*Attorney, Agent, or Firm*—Wenderoth, Lind & Ponack

[57] ABSTRACT

Aromatic tetracarboxylic acids or derivatives thereof of the general formula I

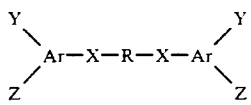

in which R denotes a divalent radical of the formula II

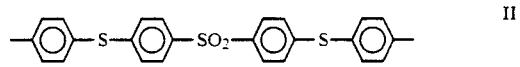

Ar denotes tri- or tetravalent aromatic radicals or mixtures thereof, X, if Ar is trivalent, denotes an amide radical, and if Ar is tetravalent denotes an imide radical, and Y and Z either together denote the anhydride radical —CO—O—CO— or by themselves and independently of one another denote the radicals —COOH, —COCL or —COOR$_1$, and a process for their preparation.

7 Claims, No Drawings

SULFUR-CONTAINING AROMATIC TETRACARBOXYLIC ACIDS AND DERIVATIVES THEREOF

The invention describes novel sulfur-containing aromatic tetracarboxylic acids and derivatives thereof and processes for their preparation.

Tetracarboxylic acid dianhydrides, such as, for example, pyromellitic acid dianhydride or benzophenonetetracarboxylic acid dianhydride, are used in industry, for example, for the preparation of polymers which are particularly heat-stable, that is to say the polyimides. Aromatic polyimides can be prepared, for example, in 2 stages by polyaddition and polycondensation. In the first stage, an aromatic diamine is subjected to polyaddition with an aromatic tetracarboxylic acid dianhydride to give the polyamide acid. In this form, the polymers are still readily soluble and can be processed, for example, to films and fibers. In the second stage, intramolecular cyclization takes place by removal of water by means of heat or chemically to give the insoluble polyimide which has a high heat stability (Macromol.Revs., 11 (1976) 161–208). Since, to a small extent, the polyamide acid converts to insoluble polyimide even at noon temperature, and hence the content of soluble polyamide acid reduces as the time increases, the polyamide acid solutions have only a limited shelf life.

Although the polyimides consisting exclusively of aromatic units have a high heat stability, they are completely insoluble and non-fusible and can thus be processed only with difficulty (J.Polym.Sci., A3 (1965) 1373–1390). This difficult processability makes the polyimides quite considerably more expensive and therefore excludes them from a number of interesting uses.

Soluble and/or fusible polyimides which are therefore easier to process can be obtained by changes to the chemical structure of the aromatic basic units, for example by incorporation of flexible chain elements ($-CH_2-$, $-O-$, $-S-$ or $-CO-$) or sterically bulky groups, but these products generally have a lower heat stability (J.Appl.—Polym.Sci., 26 (1981) 3837–3843). The polyamidoimides, which are prepared, for example, from aromatic tricarboxylic acid monoanhydrides and aromatic diamines, are products with a comparable profile of properties (U.S. Pat. No. 3,895,064). They are also soluble in polar organic solvents and usually have thermoplastic properties, but likewise have a lower heat stability in comparison with the aromatic polyimides.

The object of the present invention was to develop tetracarboxylic acids or derivatives thereof from which, for example, polyimides or polyamidoimides can be prepared by polyaddition with suitable diamines and subsequent cyclization, these products have an extreme heat stability and being soluble and/or fusible in the cyclized form and thus easily processable by conventional methods.

It has now been found that this object can be achieved with the aid of tetracarboxylic acids or derivatives thereof having aromatic, flexible chain elements containing $-S-$ and $-SO_2-$ bridges.

The present invention accordingly relates to aromatic tetracarboxylic acids or derivatives thereof of

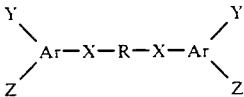

in which R denotes a divalent radical of the formula II:

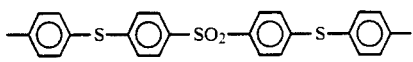

Ar denotes tri- or tetravalent aromatic radicals which are optionally substituted by one or more halogen atoms or mixtures thereof, it additionally being possible for the trivalent aromatic radical optionally to contain a, carboxyl group as a substituent, X, if Ar is trivalent, denotes the radical $-CO-NH-$, and if Ar is tetravalent denotes the imide radical of the formula III:

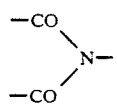

in which N is in each case bonded to R, an Y and Z either together denote the anhydride radical $-CO-O-CO-$ or by themselves and independently of one another denote the radicals $-COOH$, $-COCl$ or $-COOR_1$, in which $R_1$ represents an alkyl radical having 1–20 C atoms or an aryl radical having 6 to 20 C atoms.

All the known tri- or tetravalent aromatic radicals Ar which are derived, in particular, from the corresponding tri- or tetracarboxylic acids or their derivatives, such as, for example, anhydrides, esters or acid chlorides, are possible according to the invention. Examples of these are radicals of aromatics, fused aromatics, heteroaromatics and derivatives thereof.

Aromatic tetracarboxylic acids or derivatives thereof of the formula I:

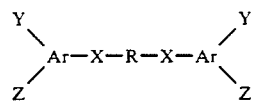

which contain a benzene or benzophenone radical as the aromatic radical Ar are preferred. The aromatic can also be substituted.

If the trivalent radical Ar additionally contains a carboxyl group as a substituent, that is to say is derived from a tetracarboxylic acid or derivative thereof, the tetracarboxylic acid derivative of the formula I of the formula according to the invention:

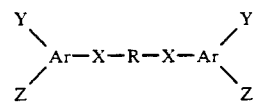

is in the form of a bis-amide acid corresponding to the formula VII:

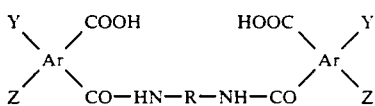

in which Y and Z have the above meaning.

In the case of the aromatic tetracarboxylic acid esters of the formula I:

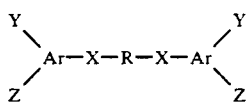

$R_1$ preferably represents a lower radical having 1 to 6 C atoms or a benzene radical.

The aromatic tetracarboxylic acids according to the invention or derivatives thereof can be prepared by reacting tricarboxylic acid monoanhydride chlorides or tetracarboxylic acid dianhydrides or mixtures thereof of the formula IV:

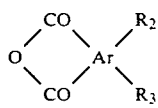

in which, in the case of the tricarboxylic acid monoanhydride-chlorides, $R_2$ stands for H and $R_3$ stands for —COCl, and in the case of the tetracarboxylic acid dianhydrides, $R_2$ and $R_3$ together stand for the anhydride radical —CO—O—CO—, with the diamine of the formula V:

(preparation, for example, in accordance with EP-A-0,245,815), in which R has the above meaning, in a molar ratio of at least 2:1 in a manner which is known per se, the tetracarboxylic acid dianhydrides of the formula I:

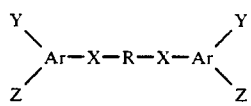

in which X denotes the radical —CO—NH— being formed in the case where the tricarboxylic acid monoanhydride-chlorides of the formula IV:

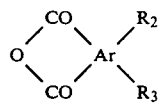

are used, and the bis-amide acid dianhydrides of the formula VI:

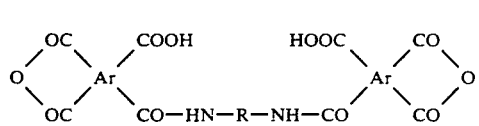

initially being formed in the case where the tetracarboxylic acid dianhydrides of the formula IV:

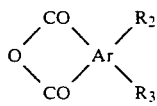

are used, if appropriate cyclizing these products chemically or by means of heat to give the tetracarboxylic acid dianhydrides of the formula I:

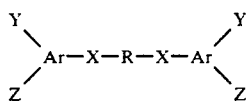

in which X denotes the imide of the formula III:

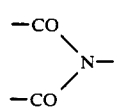

and then if appropriate partly or completely reacting the tetracarboxylic acid dianhydrides formed, of the general formula I, with water, alcohols, and/or hydrochloric acid in a manner which is known per se to give the corresponding acids, acid chlorides or esters of the general formula I.

The reaction of the tri- or tetracarboxylic acid derivatives of the formula IV:

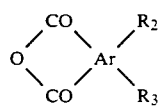

with the diamine of the formula V:

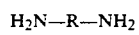

can be carried out in a manner which is known per se in strongly polar solvents, such as, for example, dimethylformamide (DMF), dimethylacetamide (DMA), N-methylpyrrolidone (NMP), dimethyl sulfoxide (DMSO), tetramethylurea or hexamethylphosphoric acid triamide. An HCl-trapping agent, for example a tertiary amine, is advantageously added during the reactions of the tricarboxylic acid monoanhydride-chlorides.

The tetracarboxylic acids according to the invention or derivatives thereof can be isolated either by distilling off the solvent (in the case of batch 1:1) or by precipitation (for example in benzene) with subsequent recrystallization (for example from acetic anhydride).

If the two partners are used in exactly the stoichiometric ratio of 2:1, the intermediately formed solutions of the tetracarboxylic acids or derivatives thereof as the formula I:

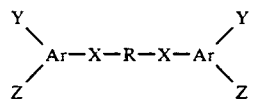

can also be used for further reactions—for example polyreactions with aromatic diamines—without being isolated.

The reaction temperature can be varied within a wide range depending on the starting substances used and the desired end product. If the anhydride-chlorides are used, such as, for example, trimellitic acid anhydride-chloride, the reaction temperatures are between $-50°$ and $+30°$ C., and when the tetracarboylic acid derivatives are used they are between $0°$ and $+130°$ C., and when the reaction has ended the initially resulting bis-amide acids are advantageously cyclized, for example chemically, for example by means of acetic anhydride at temperatures between $100°$ and $150°$ C., without being isolated.

Benzophenonetetracarboxylic acid dianhydride, pyromellitic acid dianhydride or trimellitic acid anhydride-chloride is preferably used for the synthesis of the tetracarboxylic acids according to the invention or derivatives thereof. According to the invention, however, other tetracarboxylic acid dianhydrides, thus, for example, 4,4',5,5',6,6'-hexafluorobenzophenone-2,2',3,3'-tetracarboxylic acid dianhydride, 3,3',4,4'-diphenyl-tetracarboxylic acid dianhydride, 2,2',3,3'-diphenyl-tetracarboxylic acid dianhydride, bis(2,3-dicarboxyphenyl)-methane-dianhydride, bis(3,4-dicarboxyphenyl)methane-dianhydride, 2,2-bis(3,4-dicarboxyphenyl)propane-dianhydride, 2,2-bis(2,3-dicarboxyphenyl)propane-dianhydride, bis(3,4-dicarboxyphenyl) ether-dianhydride, bis (2,3-dicarboxyphenyl) ether-dianhydride, bis(3,4-dicarboxyphenyl) sulfone-dianhydride, bis(3,4-dicarboxyphenyl)-phenylphosphonate-dianhydride, 3,3',4,4'-tetracarboxybenzoyloxybenzene-dianhydride, 1,4,5,8-naphthalene-tetracarboxylic acid dianhydride, 2,3,6,7-naphthalene-tetracarboxylic acid dianhydride, 1,2,5,6-naphthalene-tetracarboxylic acid dianhydride, 2,3,6,7-tetrachloronaphthalene-1,4,5,8-tetracarboxylic acid dianhydride, phenanthrene-1,8,9,10-tetracarboxylic acid dianhydride, 3,4,9,10-perylene-tetracarboxylic acid dianhydride, thiophene-2,3,4,5-tetracarboxylic acid dianhydride, pyrazine-2,3,5,6-tetracarboxylic acid dianhydride and pyridine-2,3,5,6-tetracarboxylic acid dianhydride, can also be reacted with the diamine of the formula V:

$$H_2N-R-NH_2 \qquad V$$

Instead of trimellitic acid anhydride-chloride, it is also possible for another known tricarboxylic acid monoanhydride-chlorides, thus, for example, 4-(4-(chlorocarbonyl) phenoxy)phthalic anhydride, 4-(4-(chlorocarbonyl)-benzoyl) phthalic anhydride, 4-(4-chlorocarbonyl)-phenylsulfonyl) phthalic anhydride and 4-(4-(chlorocarbonyl)-benzyl) phthalic anhydride, to be reacted with the diamine of the formula V:

$$H_2N-R-NH_2 \qquad V$$

EXAMPLE 1

Reaction of 1,4-bis(4-aminophenylthio)diphenyl sulfone (BDS) with trimellitic anhydride-chloride (TMACl)

Batch:
10.85 g (0.05 mol) of TMACl
9.30 g (0.02 mol) of BDS
90 ml of absolute N-methyl-2-pyrrolidone (NMP)

The apparatus consists of a 250 ml three-necked flask with a mechanical stirrer, thermometer, dropping funnel with drying tube and nitrogen inlet tube and is heated with a flame in a dry stream of nitrogen. The TMACl is dissolved in 25 ml of NMP, the solution is cooled to $-40°$ C. with dry ice/acetone and the BDS in 65 ml of NMP is added dropwise at this temperature in the course of 30 minutes. After a further 30 minutes at $-40°$ C., the reaction mixture is heated slowly to room temperature and is then stirred for a further 3 hours.

The resulting viscous solution is added dropwise to 500 ml of absolute benzene at $10°$ C., while excluding atmospheric moisture and while stirring, until after about 1 hour a pale yellow precipitates separates out, which is filtered off, washed with cold and hot absolute benzene and then dried at $60°$ C. in a vacuum drying cabinet. The crude product is recrystallized from absolute acetic anhydride.

Yield: 14.7 g (90% of theory), melting point: $282°$–$288°$ C.

| | Analysis: | |
|---|---|---|
| | calculated (%) | found (%) |
| $C_{42}$ | 62.05 | 61.62 |
| $H_{24}$ | 2.98 | 3.16 |
| $N_2$ | 3.45 | 3.56 |
| $S_3$ | 11.83 | 12.24 |
| $O_{10}$ | | |

EXAMPLE 2

Reaction of BDS with Benzophenonetetracarboxylic Acid Dianhydride (BTDA)

Batch:
6.4446 g (0.02 mol) of BTDA
4.6464 g (0.01 mol) of BDS
(3.6 g (0.035 mol) of acetic anhydride
60 ml of absolute dimethylacetamide (DMA)

The BTDA is dissolved in 25 ml of DMA in a dry apparatus consisting of a 100 ml three-necked flask, magnetic stirrer, reflux condenser, dropping funnel, nitrogen inlet tube, thermometer and drying tube. The BDS, dissolved in 35 ml of DMA, is added dropwise at room temperature in the course of 15 minutes and the reaction mixture is heated to $90°$ C. After 30 minutes, 3.6 g of acetic anhydride are added and the temperature is increased to $125°$ C. for 1 hour. The dark brown solution is evaporated on a rotary evaporator and the residue is recrystallized from absolute acetic anhydride and then dried in a vacuum drying cabinet at $90°$ C.

Yield: 9.5 g (88% of theory), melting point $238°$–$242°$ C.

| | Analysis: | |
|---|---|---|
| | calculated (%) | found (%) |
| $C_{58}$ | 64.92 | 64.37 |
| $H_{28}$ | 2.64 | 2.92 |
| $N_2$ | 2.61 | 2.39 |
| $S_3$ | 8.96 | 8.76 |
| $O_{14}$ | — | — |

EXAMPLE 3

Esterification of the dianhydride obtained in Example 2

Batch:

2.15 g (0.002 mol) of dianhydride
20 ml of absolute butanol
10 ml of absolute pyridine
25 ml of absolute DMA The dianhydride is boiled under reflux in a mixture of butanol, pyridine and DMA. After 6 hours, the reaction mixture is poured onto 5% strength NaCl solution and the ether which has precipitated is filtered off and dried at 60° C., in a vacuum drying cabinet.

Yield: 2.11 g (89% of theory), melting point: 273°–278° C.

| | Analysis: | |
|---|---|---|
| | calculated (%) | found (%) |
| $C_{66}$ | 64.90 | 64.63 |
| $H_{48}$ | 3.97 | 4.28 |
| $N_2$ | 2.29 | 2.06 |
| $S_3$ | 7.87 | 7.54 |
| $O_{16}$ | | |

EXAMPLE 4

Reaction of BDS With Pyromellitic Acid Dianhydride (PMDA)

Batch:
9.597 g (0.44 mol) of PMDA
9.293 g (0.02 mol) of 1.4-bis(4-aminophenylthio)-diphenyl sulfone (BDS)
7.2 g (0.07 1 mol) of absolute acetic anhydride
100 ml of absolute DMA The PMDA is dissolved in 35 ml of DMA in a dry apparatus consisting of a 250 ml three-necked flask, magnetic stirrer, reflux condenser, dropping funnel, nitrogen inlet tube, thermometer and drying tube. The BDS, dissolved in 65 ml of DMA, is added dropwise at room temperature in the course of 15 minutes and the reaction mixture is heated to 90° C. After 30 minutes, 7.2 g of acetic anhydride are added and the temperature is increased to 125° C. for 1 hour. The resulting viscous solution is added dropwise to 500 ml of absolute benzene at 10° C., while excluding atmospheric moisture and while stirring, and the yellow precipitate which has separated out is filtered off, washed with cold and hot absolute benzene and then dried at 60° C. in a vacuum drying cabinet. The crude product is recrystallized from absolute acetic anhydride.

Yield: 14.4 g (83% of theory), melting point: 256°–261° C.

| | Analysis: | |
|---|---|---|
| | calculated (%) | found (%) |
| $C_{44}$ | 61.11 | 60.83 |
| $H_{20}$ | 2.33 | 2.57 |
| $N_2$ | 3.24 | 3.03 |
| $S_3$ | 11.12 | 10.98 |
| $O_{12}$ | — | — |

EXAMPLE 5

Hydrolysis of the dianhydride obtained in Example 4

Batch:
1.73 g (0.002 mol) of dianhydride
100 ml of 0.01 N HCL

The dianhydride is boiled under reflux in 0.01N HCl for 4 hours. The resulting tetracarboxylic acid is filtered off and dried in a vacuum drying cabinet at 70° C.

Yield: 1.74 g (97% of theory), melting point: 248°–252° C.

| | Analysis: | |
|---|---|---|
| | calculated (%) | found (%) |
| $C_{44}$ | 58.79 | 58.52 |
| $H_{24}$ | 2.47 | 2.79 |
| $N_2$ | 3.12 | 2.86 |
| $S_3$ | 10.70 | 10.42 |
| $O_{14}$ | | |

We claim:

1. An aromatic tetracarboxylic acid or derivative thereof of the formula I $$\begin{matrix} Y & & Y \\ \diagdown & & \diagup \\ & Ar-X-R-X-Ar & \\ \diagup & & \diagdown \\ Z & & Z \end{matrix} \quad I$$

in which R denotes a divalent radical of the formula II $$-\phi-S-\phi-SO_2-\phi-S-\phi- \quad II$$

Ar denotes tri- or tetravalent aromatic radicals which are unsubstituted or substituted by one or more halogen atoms or mixtures thereof, it additionally being possible for the trivalent aromatic radical to contain a carboxyl group as a substituent, X, if Ar is trivalent, denotes the radical
—CO—NH—, and if Ar is tetravalent denotes the imide radical of the formula III $$\begin{matrix} -CO \\ \diagdown \\ \phantom{-CO}N- \\ \diagup \\ -CO \end{matrix} \quad III$$

in which N is in each case bonded to R, and Y and Z either together denote the anhydride radical —CO—O—CO— or by themselves and independently of one another denote the radicals —COOH, —COCl or —COOR$_1$, in which R$_1$ represents an alkyl radical having 1 to 20 C atoms or an aryl radical having 6 to 20 C atoms.

2. The aromatic tetracarboxylic acid or derivative thereof as claimed in claim 1, in which the radical Ar represents a benzophenone radical.

3. The aromatic tetracarboxylic acid or derivative thereof as claimed in claim 1, in which the radical Ar represents a benzene radical.

4. A process for the preparation of an aromatic tetracarboxylic acid or derivative thereof of the formula I $$\begin{matrix} Y & & Y \\ \diagdown & & \diagup \\ & Ar-X-R-X-Ar & \\ \diagup & & \diagdown \\ Z & & Z \end{matrix} \quad I$$

in which R denotes a divalent radical of the formula II

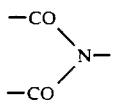 II

Ar denotes tri- or tetravalent aromatic radicals which are unsubstituted or substituted by one or more halogen atoms or mixtures thereof, it additionally being possible for the trivalent aromatic radical to contain a carboxyl group as a substituent, X, if Ar is trivalent, denotes the radical —CO—NH—, and if Ar is tetravalent denotes the imide radical of the formula III

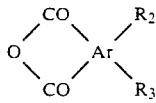 III in which N is in each case bonded to R, and Y and Z either together denote the anhydride radical —CO—O—CO— or by themselves and independently of one another denote the radicals —COOH, —COCl or —COOR$_1$, in which R$_1$ represents an alkyl radical having 1 to 20 C atoms or an aryl radical having 6 to 20 C atoms, which comprises reacting a tricarboxylic acid monoanhydride-chloride or tetracarboxylic acid dianhydride or mixture thereof of the formula IV

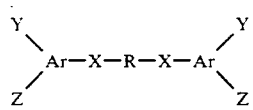 IV in which, in the case of the tricarboxylic acid monoanhydride-chloride, R$_2$ stands for H and R$_3$ stands for —COCl, and in the case of a tetracarboxylic acid dianhydride, R$_2$ and R$_3$ together stand for the anhydride radical —CO—O—CO—, with the diamine of the formula V

H$_2$N—R—HN$_2$   V in which R has the above meaning, in a molar ratio of at least 2:1, a tetracarboxylic acid dianhydride of the formula I

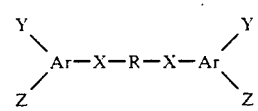 I in which X denotes the radical —CO—NH— being formed in the case where a tricarboxylic acid monoahydride-chloride of the formula IV

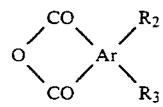 IV is used, and a bis-amide acid dianhydride of the formula VI

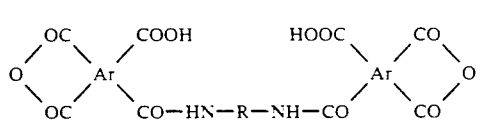 VI initially being formed in the case where a tetracarboxylic acid dianhydride of the formula IV

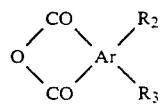 IV is used, or further cyclizing the products chemically or by means of heat to give a tetracarboxylic acid dianhydride of the formula I

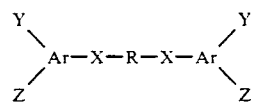 I in which X denotes the imide radical of the formula III

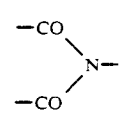 III and or further subsequently completely or partly reacting the tetracarboxylic acid dianhydride formed, of the formula

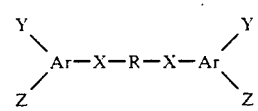 I with water, an alcohol and/or hydrochloric acid to give the corresponding acid, acid chloride or ester of the formula I

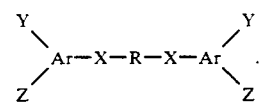 I

5. The process as claimed in claim 4, wherein trimellitic acid anhydride-chloride is used as the tricarboxylic acid monoanhydride-chloride.

6. The process as claimed in claim 4, wherein pyromellitic acid dianhydride is used as the tetracarboxylic acid dianhydride.

7. The process as claimed in claim 4, wherein benzophenonetetracarboxylic acid dianhydride is used as the tetracarboxylic acid dianhydride.

* * * * *